(12) United States Patent
Fleming

(10) Patent No.: US 7,305,992 B2
(45) Date of Patent: Dec. 11, 2007

(54) CONFORMING EARPLUG

(75) Inventor: Thomas W. Fleming, San Diego, CA (US)

(73) Assignee: Howard Leight Industries, LLC, San Diego, CA (US)

( * ) Notice: Subject to any disclaimer, the term of this patent is extended or adjusted under 35 U.S.C. 154(b) by 181 days.

(21) Appl. No.: 10/778,658

(22) Filed: Feb. 13, 2004

(65) Prior Publication Data
US 2004/0163653 A1    Aug. 26, 2004

Related U.S. Application Data

(60) Provisional application No. 60/450,184, filed on Feb. 25, 2003.

(51) Int. Cl.
*A61F 11/00* (2006.01)
(52) U.S. Cl. ............... 128/864; 181/129; 181/130; 181/134
(58) Field of Classification Search ............. 128/864, 128/867, 868, 865; 181/128, 129, 130, 134, 181/135
See application file for complete search history.

(56) References Cited

U.S. PATENT DOCUMENTS

| | | | |
|---|---|---|---|
| 4,867,149 A | 9/1989 | Falco | |
| 4,936,411 A | 6/1990 | Leonard | |
| 5,792,998 A | 8/1998 | Gardner, Jr. et al. | |
| 5,957,136 A * | 9/1999 | Magidson et al. | 128/864 |
| 6,241,041 B1 | 6/2001 | Leight | |
| 6,695,093 B1 * | 2/2004 | Falco | 181/135 |

FOREIGN PATENT DOCUMENTS

| | | |
|---|---|---|
| EP | 0955025 | 11/1999 |
| WO | WO 98/31313 | 7/1998 |
| WO | WO 01/50993 A1 | 7/2001 |

* cited by examiner

*Primary Examiner*—Patricia Bianco
*Assistant Examiner*—Camtu Nguyen
(74) *Attorney, Agent, or Firm*—Leon D. Rosen

(57) ABSTRACT

An earplug of the type that has a stem (12) and a plurality of flanges (21–23), is constructed to be stiff enough to be easily inserted into the ear canal, and to thereafter press with minimal force against the walls of the ear canal for comfort. The earplug is molded of an elastomeric material whose stiffness decreases considerably, such as at least 4%, when it is warmed from room temperature (about 72° F.) to ear canal temperature (about 100° F.). Each flange has a radially inner portion (52) that extends straight at an angle (B) that is within 15° of a radial direction (62) (a direction perpendicular to the stem axis), and has a radially outer portion (54) that extends straight and at an angle (C) that is within 20° of an axial direction (66).

12 Claims, 2 Drawing Sheets

US 7,305,992 B2

CONFORMING EARPLUG

CROSS-REFERENCE

Applicant claims priority from U.S. Provisional Patent Application No. 60/450,184 filed Feb. 25, 2003.

BACKGROUND OF THE INVENTION

One type of earplug in widespread use, is formed of solid soft-rubber type material, and is integrally molded with a stem and flanges. The flanges extend from the stem and are easily deflected as the stem is inserted into the ear canal. Earplugs with soft rubber flanges are commonly formed of material having a durometer of between 1 Shore A and 50 Shore A, and usually with a durometer of about 30 Shore A. A higher durometer (stiffer material) results in a stiffer stem, which enables the earplug to be more easily pushed into the ear canal. A lower durometer (softer material) results in flanges that are more easily deflected by the ear canal and result in greater comfort. If a stiff material is used, the flanges will press harder against the ear canal and create discomfort. If a soft material is used, then when the stem is pushed forward to insert the earplug into the ear canal, the stem tends to buckle, or undergo column collapse. A solid soft-rubber type earplug molded with a stem and integral flanges, in which the stem was stiff during insertion and the flanges were soft while the earplug was worn, would be of value.

SUMMARY OF THE INVENTION

In accordance with one embodiment of the present invention, an earplug is provided, of the type that is molded of elastomeric material with a stem extending along an axis and with flanges extending from the stem, wherein the stem is stiff during insertion into the ear canal and the flanges are soft while the plug is worn. The earplug is molded of a material that undergoes a substantial decrease in stiffness, by a decrease of at least one Shore A number or at least 4% in Shore A number, when it is warmed from room temperature of about 70° to 72° F. to ear canal temperature of about 98° to 100° F. Thus, the stem is stiffer during insertion into the ear canal at room temperature, and the flanges become softer after insertion by warming from heat of the ear canal. One material is a styrene block copolymer.

Each flange preferably has a radially inner portion that extends primarily radially with respect to the stem axis, at an angle of no more than 15° to the radial. Each flange has a radially outer portion that extends straight and primarily axially, at a rearward and radially outward incline angle of less than 20° to the axial direction. The substantially radially-extending inner portion takes up very little of the limited axial length of the earplug front portion, thereby allowing the outer flange portion to extend a considerable distance at a small incline. The small incline assures good sound sealing with minimal deflection of the flanges for increased comfort.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
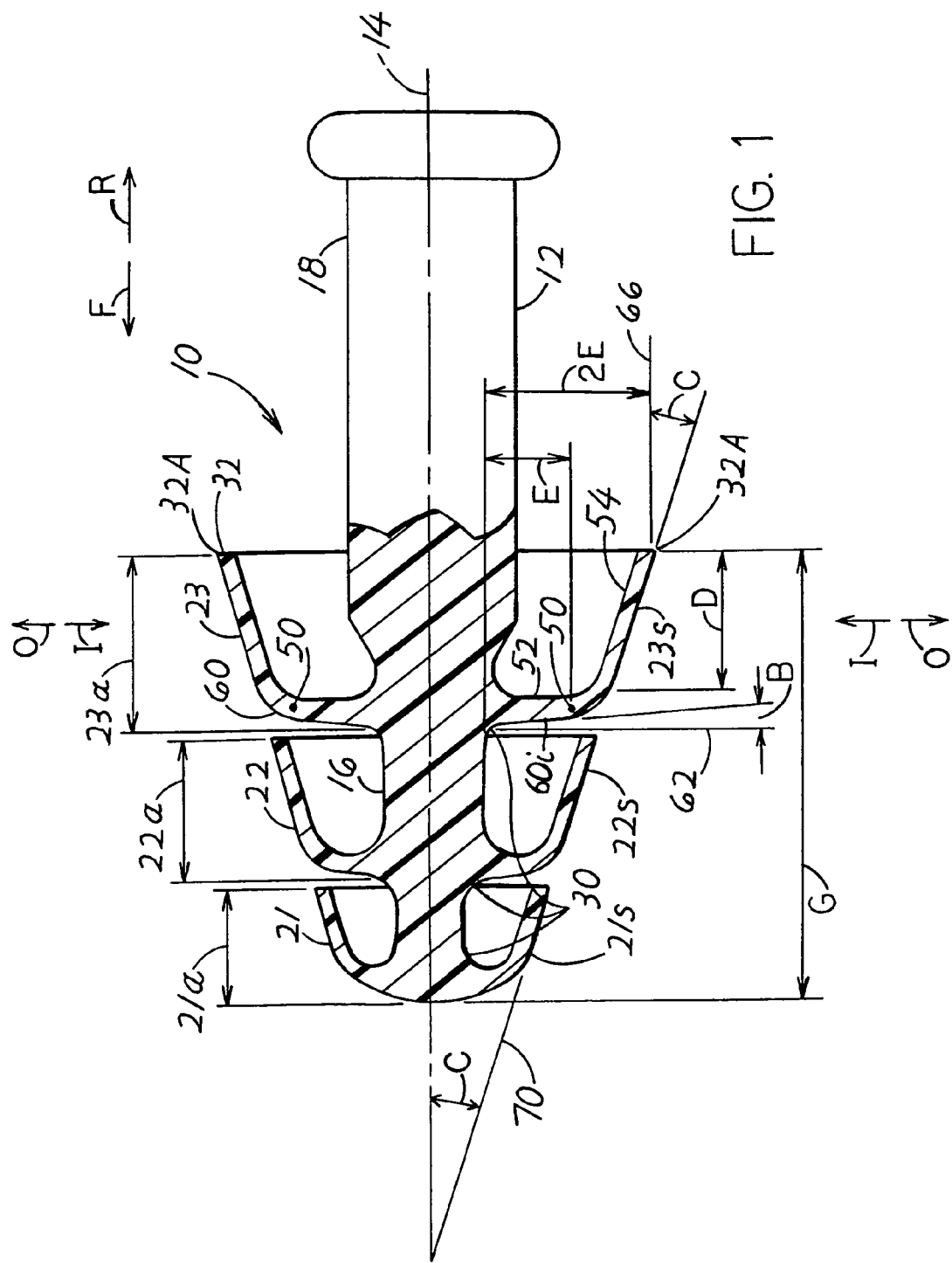
FIG. 1 is a partially sectional side view of an earplug of the present invention.

FIG. 1 is a sectional view of an earplug 10 of the present invention, which includes a stem 12 that extends in forward F and rearward R directions along a stem and earplug axis 14. The stem has forward and rearward portions 16, 18. The forward portion carries three flanges 21–23 that seal to the walls of a person's ear canal. The stem rearward portion 18 serves as a handle to push the flanges into the ear canal and later pull them out. The flanges are thin, have radially inner ends 30 that merge (at their forward surfaces) with the stem, and have free radially outer ends 32.

The stem and flanges are integrally molded, and generally of the same elastomeric material, such as a material having a durometer of 30 Shore A. An elastomeric material is a material having a Young's modulus of elasticity of no more than 50,000 psi. It would be desirable to mold the stem of a stiffer material (higher durometer number) to facilitate insertion into the ear canal, and to mold the flanges of softer material (lower durometer number) so the flanges press with less force against the ear canal to increase comfort. However, it has previously not been possible to achieve this at low cost.

In accordance with the present invention, applicant molds the earplug of an elastomeric material whose durometer number changes, between the time when an earplug is initially inserted into the ear canal and a time that is perhaps a minute later. Applicant uses a material whose durometer number decreases significantly when the temperature of the material increases from a room temperature such as 72° F. to body temperature such as 100° F. that exists in the human ear canal. If the ear plug has been lying in a room at room temperature (e.g. 72° F.), it will have a predetermine stiffness such as 30 Shore A which provides sufficient stem stiffness to insert the flanges into the ear canal without the stem collapsing. The flanges initially will not be comfortable. However, after the flanges lie in the person's ear canal for perhaps one minute, the temperature of the flanges will increase to close to body temperature (about 100° F.). The stiffness of the earplug material will decrease to a durometer of perhaps 26 Shore A, so that the flanges will press with less force against the ear canal and the ear plug will be more comfortable. In industrial applications, the earplugs may be worn for perhaps 110 minutes at a time, and some discomfort for the first minute or so can be easily tolerated.

Figure 2:
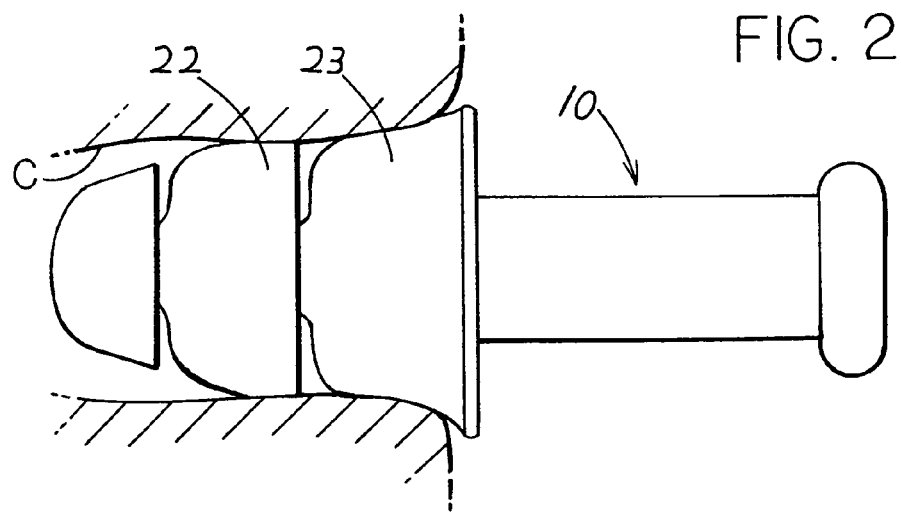
FIG. 2 is a side view the earplug of FIG. 1, shown inserted into a person's ear canal.

The particular earplug 10 shown in FIG. 1 is formed of styrene block copolymer (SBC) elastomer, using a blend of a lower glass transition temperature SBC (e.g. −60° C. to −75° C.) and of a higher glass transition temperature SBC (e.g. −25° C. to −10° C.). Applicant has constructed an earplug of the construction illustrated in FIGS. 1–3 and found that the material results in an earplug that is relatively easy to insert into the ear canal, and that results (after a minute or so) in less pressure against the ear canal and therefore greater comfort. After inserting the earplug into the ear canal and waiting for perhaps 30 minutes, applicant pulled out the earplug and found that the outside diameter of its flanges (or at least the flanges that entered the ear canal and were deflected to a smaller diameter) were reduced somewhat. However, within much less than 30 minutes, when the earplug had cooled to room temperature, the flanges had returned to their original sizes and shapes. The blend of SBC elastomer materials of different transition temperatures which results in such sustained compression at 100° F. (e.g. a largest flange 23 diameter decrease from 12.5 mm to 12 mm) provides further comfort.

Further tests on the earplugs show that the durometer of the earplug material decreases as the material is heated from about 72° F. to about 100° F. in the ear. The decrease in durometer (from 30 Shore A at 72° F.) is more than one out of 30 (i.e. more than 3.3%), and the durometer at 100° F. is actually about 26 Shore A. As a result, the stem is fairly stiff when the earplug (at 72° F.)is inserted, which makes insertion possible without collapsing of the stem. However, once the earplug is inserted the durometer decreases, resulting in softer flanges that press with less force against the ear canal, and resulting greater comfort. For an increase in temperature from 72° F. to 100° F., the durometer should decrease by at least one Shore A number and by at least 4%, preferably should decrease by at least two Shore A numbers and by at least 8%, and most preferably should decrease by at least three Shore A numbers and at least 10%.

Not only is the durometer of the material decreased, but the material appears to temporarily deform, since the outside diameter of the flanges is found to have decreased when measured immediately after the earplug is taken out on the ear canal. This results in the flanges pressing with even less force against the walls of the ear canal. However, the material appears to have a memory, in that when the earplug is taken out of the ear canal and the earplug slowly cools to room temperature, the outside diameter of the flanges returned to the original diameter that existed prior to first insertion.

Thus, the above styrene block copolymer elastomer reduces pressure of the flanges against the ear canal, apparently in two ways. One way is by undergoing a decrease in durometer as its temperature increases from room temperature to body temperature. The second way in which the material aids in comfort, is by undergoing a temporary decrease in flange undeflected outside diameter when deflected and warmed, with the material appearing to have a memory in that the flange diameter returns to its original diameter when the earplug is removed from the ear canal and cools to room temperature. As a further benefit, applicant finds that the above described SBC material is a better blocker of noise than previous materials such as polybutadiene rubber, polyurethane elastomer, or ethylene vinyl acetate elastomer that have been used for flanged earplugs.

Figure 3:
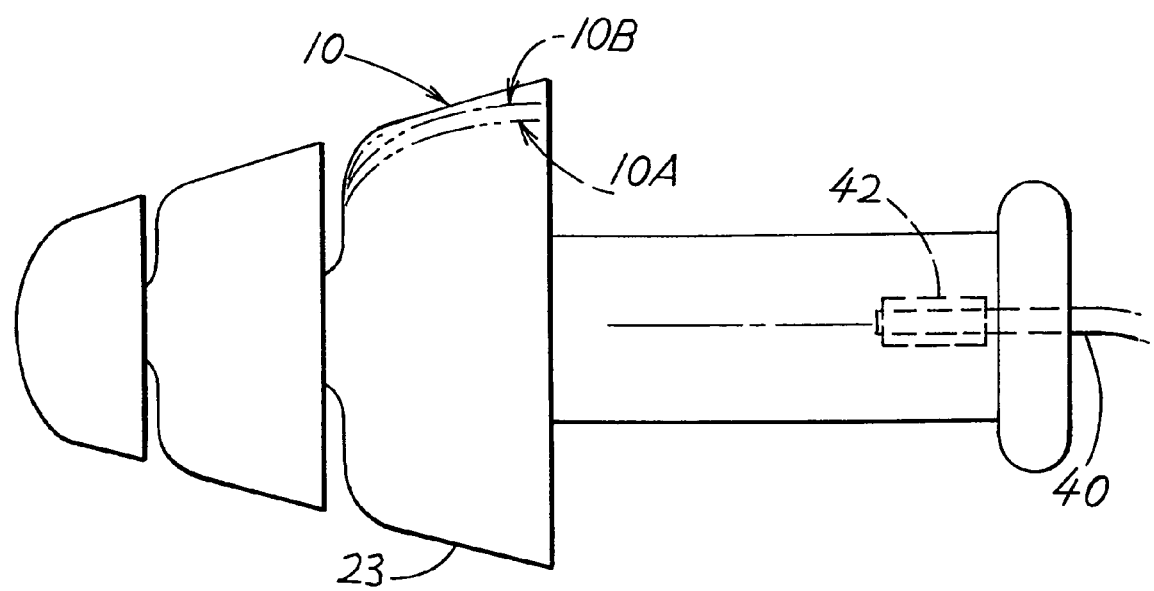
FIG. 3 is an enlarged side view of the earplug of FIG. 1, showing in phantom lines how a fully inserted flange is deflected, and showing a cord end installed in the stem.

FIG. 3 is an enlarged view of the earplug, showing the original shape at 10, the deformed shape at 10A of the outer surface of flange 23 when lying in the ear canal, and the partially recovered shape at 10B after the earplug is removed from the ear, but before the flanges have cooled down from ear temperature to room temperature. FIG. 3 also shows a cord 40 with a metal ferrule 42 at the end(which can be detected by a metal detector), that has been inserted into the rear end of the earplug. The cord 40 is long enough to extend loosely behind the head of a person while holding the two earplugs together.

Flange 23 of FIG. 1 has radially inner and outer flange ends 30, 32, and has a middle 50 that lies radially halfway between the opposite ends 30, 32. Radial directions are directions perpendicular to the axis 14. Radial distances E and 2E of the flange front surface, from the stem to the radial midpoint 50 and from the stem to the outer end of the outer surface 32A, are shown. The flange 23 also has inner and outer portions 52, 54. The inner flange portion 52 extends from the inner flange portion inner end 30 by at least 40% of the flange radial length 2E and preferably all the way to the flange middle 50, and the outer flange portion 54 extends from the flange middle 50 to the flange free outer end 32A. The front surface 60 of the flange has an inner front surface portion 60i along the inner flange portion 52, that extends within an angle B of 15° from a direction 62 that is directly radial to the axis 14, along a majority of the radial length of the inner flange portion 52. The angle B is preferably no greater than 10°, and the actual angle B of the constructed earplug is about 5°. The outer flange portion 54 extends straight and at a rearward R and radially outward O incline C, that is within 20° of an imaginary line 66 that extends parallel to the axis 14, between points 68 and 32A. For purposes of explanation, points along the cross-section are referred to instead of circles around the axis, although each flange and the stem are 360° symmetric about the axis 14.

By applicant extending the radially inner portion 52 of the flange close to a directly radial direction, applicant places the flange outer portion 54 close to the ear canal. As a result, the outer portion 54 can extend primarily straight and at a small angle C to the axial direction along a considerable flange axial length D which is at least half and preferably at least two-thirds of the axial length of the flange outer portion 54. The actual length D in FIG. 1 is 77% of the entire flange axial length 23a. The largely axially-extending outer portion 54 forms a good sound-tight seal against the ear canal. The other flanges, especially flange 22, are preferably of the same design (but of slightly smaller diameter) as flange 23. The axial length G of the three flanges is about 15 millimeters, which is about the length of earplug that enters the ear canal. Applicant's outer flange portions 54 can extend at least two-thirds (67%) of this length within about 20° of the axial direction.

The three flanges 21–23 have outer flange surfaces 21s, 22s, 23s that lie along a single imaginary line 70 that is angled by an angle C of 17° (no more than 20°) from the axis, which facilitates construction. The straight outer flange surfaces 21s, 22s, 23s preferably extend no more than 25° to the axis, and each preferably occupies at least two-thirds the axial length 21a, 22a, 23a of each flange. The entire outer flange surfaces of the three flanges lie along an imaginary cone with line 70 lying on the imaginary cone.

Thus, the invention provides an earplug of the type that has a stem, and that has at least one flange (23) and preferably a plurality of flanges that extend from a front portion of the stem, which provides a stiff stem to facilitate insertion of the flanges and that provides flanges of reduced stiffness (after perhaps a minute) for increased comfort. This is accomplished by molding the earplug of a material whose stiffness decreases with increasing temperature, so the stiffness decreases appreciably when the temperature rises from a room temperature of about 72° F. to body temperature of about 100° F. More efficient flanges are obtained by constructing each flange so its radially inner portion, or radially inner half as measured outward from the stem, extends within a small angle (e.g. within 15°) of a radial direction and by constructing each flange so its radially outer portion extends straight and within a small angle (e.g. 25°) of an axial direction and so the flange portion that extends at no more than 25° to the axis, extends along at least two-thirds of the flange axial length.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug molded of an elastomeric material, which includes an axis, a rear stem portion forming a handle and a front stem portion, said earplug including at least one flange that extends from said stem front portion and that is designed to block a person's ear canal, wherein:

said flange has a radial length, as measured between the flange radially inner end where a front surface of the flange intersects the stem, and a flange radially outer end where the flange front surface is radially furthest from the axis, and said flange has a radially inner half that extends at no more that 15° to the radial direction along a majority of the radial length of said inner half;

said flange has an axial length, and said flange extends at a rearward and radially outward incline of no more than 25° along at least two-thirds of said flange axial length.

2. The earplug described in claim 1 wherein:

said earplug is molded of an elastomeric material whose durometer Shore A number decreases by at least 4% when the temperature of the material is raised from 72° F. to 100° F.

3. The earplug described in claim 2 wherein:

said elastomeric material undergoes a decrease in durometer Shore A number of at least 8% when its temperature increases from 72° F. to 100° F.

4. The earplug described in claim 1 wherein said at least one flange includes a plurality of flange devices that include said flange, and wherein:

each of said flange devices extends at a rearward and radially outward incline, along a common imaginary cone.

5. An earplug molded of an elastomeric material, which includes an axis, a rear stem portion forming a handle and a front stem portion, said earplug including at least one flange that extends from said stem front portion and that is designed to block a person's ear canal, wherein:

said flange has an axial length, as measured between the flange front end where a front surface of the flange intersects the stem, and a flange free rear end;

said flange extends at a rearward and radially outward incline of no more than 25° along a distance of at least two-thirds of said flange axial length.

6. The earplug described in claim 5 wherein:

said flange extends at a rearward and radially outward incline of no more than 20° along the rearward two-thirds of the flange entire axial length.

7. The earplug described in claim 5 wherein:

said flange has a radial length, as seen in a sectional view taken on the axis, and said stem extends within 20° of an axial direction along the radially innermost 40% of the flange.

8. The earplug described in claim 5 wherein:

said elastomeric material undergoes a decrease in durometer Shore A number of at least 8% when its temperature increases from 72° F. to 100° F.

9. An earplug molded of an elastomeric material, which includes a stem extending along an axis and having front and rear stem portions, said earplug including at least one flange extending from said stem front portion, said flange having a radially outer portion that extends largely rearwardly and which is designed to block a person's ear canal, wherein:

said at least one flange has radially inner and outer flange ends and a flange radial middle that lies radially halfway between said inner and outer flange ends, and said at least one flange has radially inner and outer flange portions, said inner flange portion extending from said inner flange end to said flange radial middle and said outer flange portion extending from said flange radial middle to said outer flange end;

said inner flange portion has a front surface that extends within 15° to a direction radial to said axis, along a majority of the radial length of said inner flange portion, whereby to allow said outer flange portion to extend primarily axially along most of the axial length of the flange.

10. An earplug molded of an elastomeric material, which includes a stem extending along an axis and having front and rear stem portions, said earplug including at least one flange extending from said stem front portion, said flange having a radially outer portion that extends largely rearwardly and which is designed to block a person's ear canal, wherein:

said at least one flange has radially inner and outer flange ends and a flange middle that lies radially halfway between said ends, and said at least one flange has radially inner and outer flange portions, said inner flange portion extending from said inner flange end to said flange middle and said outer flange portion extending from said flange middle to said outer flange end;

said outer flange portion has a rearward-outward surface that extends within 25° of a direction parallel to said axis, along at least two thirds of the entire axial length of said flange.

11. An earplug which has a stem extending along an axis and having front and rear stem portions, said earplug having a plurality of flanges extending generally radially outward and rearward from said stem front portion at locations thereon that are spaced therealong, wherein:

at least one of said flanges has an axial length (23a), and extends at a rearward and radially outward incline angle (C) of no more than 20° along an axial length (D) that is at least two-thirds of said flange axial length (23a).

12. An earplug which has a stem extending along an axis and having front and rear stem portions, said earplug having a plurality of flanges extending generally radially outward and rearward from said stem front portion at locations thereon that are spaced therealong, wherein:

at least one of said flanges has a radial length, as measured between the flange radially inner end where a front surface of the flange intersects the stem, and a flange radially outer end where the front surface is radially furthest from the axis;

each of said flanges has a radially inner half that extends at no more than 15° to the radial direction along most of the radial length (E) of said inner half, and each of said flanges has a radially outer half that extends at an angle (C) of no more that 25° to the axial direction along a majority of the axial length (23a) of said flange.

* * * * *